United States Patent
Swann (10) Patent No.: US 9,518,965 B2
(45) Date of Patent: *Dec. 13, 2016

(54) FUEL SYSTEM

(71) Applicant: ROLLS-ROYCE PLC, London (GB)

(72) Inventor: Peter Swann, Nottingham (GB)

(73) Assignee: ROLLS-ROYCE plc, London (GB)

(*) Notice: Subject to any disclaimer, the term of this patent is extended or adjusted under 35 U.S.C. 154(b) by 577 days.

This patent is subject to a terminal disclaimer.

(21) Appl. No.: 13/896,690

(22) Filed: May 17, 2013

(65) Prior Publication Data

US 2013/0343958 A1 Dec. 26, 2013

(30) Foreign Application Priority Data

Jun. 22, 2012 (GB) .................................. 1211064.9

(51) Int. Cl.
| | | |
|---|---|---|
| *G01N 33/00* | (2006.01) | |
| *F02C 9/28* | (2006.01) | |
| *F02C 9/40* | (2006.01) | |
| *F02C 3/30* | (2006.01) | |

(52) U.S. Cl.
CPC ............. *G01N 33/0004* (2013.01); *F02C 3/30* (2013.01); *F02C 9/28* (2013.01); *F02C 9/40* (2013.01); *Y02T 50/671* (2013.01)

(58) Field of Classification Search
CPC ............... F02C 7/22; F02C 7/045; F02C 3/30; F02C 9/40; F02C 9/28; B64D 2033/045; F23R 3/36; G01N 33/0004
See application file for complete search history.

(56) References Cited

U.S. PATENT DOCUMENTS

| | | |
|---|---|---|
| 3,289,409 A | 12/1966 | Schirmer |
| 3,517,505 A | 6/1970 | Anderson et al. |
| 3,517,512 A | 6/1970 | Anderson et al. |
| 4,471,744 A | 9/1984 | Holtz |
| 4,766,725 A | 8/1988 | Singh |
| 5,005,355 A | 4/1991 | Singh |
| 5,285,256 A | 2/1994 | Nelson et al. |
| 5,469,830 A | 11/1995 | Gonzalez |

(Continued)

FOREIGN PATENT DOCUMENTS

| | | |
|---|---|---|
| GB | 2 058 211 A | 4/1981 |
| JP | A-61-149566 | 7/1986 |
| WO | WO 2008/065238 A1 | 6/2008 |

OTHER PUBLICATIONS

Feb. 26, 2015 Office Action issued in U.S. Appl. No. 13/896,766.

(Continued)

*Primary Examiner* — Andrew Nguyen
(74) *Attorney, Agent, or Firm* — Oliff PLC (57) ABSTRACT

A fuel system (12) comprising a vapor trail detection sensor (20) configured to generate a first signal (28) which indicates the optical depth of a vapor trail (35). A control unit (40) is provided responsive to the first signal (28) and configured to generate a second signal (80) in dependence upon the first signal (28). The second signal (80) defines a percentage of at least one of a first fuel composition and second fuel composition required to produce a resultant fuel composition. At least one regulator (42) is provided configured to receive and be responsive to the second signal (80) and regulate the percentage of first and second fuel composition required to produce the resultant fuel composition.

18 Claims, 4 Drawing Sheets

(56) References Cited

U.S. PATENT DOCUMENTS

| | | | | |
|---|---|---|---|---|
| 5,546,183 | A | * | 8/1996 | Fegley .................... G01S 17/88 356/336 |
| 5,911,210 | A | | 6/1999 | Flach |
| 2007/0175459 | A1 | * | 8/2007 | Williams ............ F02D 19/0605 123/575 |
| 2008/0072577 | A1 | | 3/2008 | Taylor et al. |
| 2009/0013591 | A1 | | 1/2009 | Bradin et al. |
| 2010/0043443 | A1 | | 2/2010 | Noppel et al. |
| 2010/0122519 | A1 | | 5/2010 | Epstein et al. |
| 2010/0132330 | A1 | * | 6/2010 | Noppel .................... F01D 25/30 60/39.5 |
| 2011/0289932 | A1 | * | 12/2011 | Thompson ................ F02C 3/30 60/776 |

OTHER PUBLICATIONS

Sep. 27, 2012 Search Report issued in British Application No. GB1211064.9.

Oct. 18, 2012 Search Report issued in British Application No. GB1211061.5.

Sep. 18, 2012 Search Report issued in British Application No. GB1211058.1.

U.S. Appl. No. 13/896,793, filed May 17, 2013 in the name of Peter Swann.

U.S. Appl. No. 13/896,766, filed May 17, 2013 in the name of Peter Swann.

* cited by examiner

FUEL SYSTEM

The present disclosure relates to a fuel system.

Vapour trails are artificial clouds that are visible trails of condensed water vapour exhausted by vehicles' engines. They may be formed as warm, moist exhaust gas mixes with ambient air, and arise from the precipitation of microscopic water droplets or, if the air is cold enough, tiny ice crystals. The term "vapour trails" is intended to refer both to condensation trails (that is to say "contrails") from aircraft and to water and/or ice precipitation in or attributable to the exhaust plumes from engines of other machines and vehicles, such as ships.

It may be undesirable for some ships to produce vapour trails in certain situations. For example, a military ship producing a vapour trail from its exhaust funnels is highly visible from the air and hence much easier to target.

It is known that, depending on the timescale considered, the climate-warming impact of aircraft exhaust vapour trails and resulting vapour trail-cirrus is of a magnitude similar to, or perhaps even greater than, that of the $CO_2$ emitted by aircraft, and therefore represents a significant element of aviation's total climate impact. It is also known that an aircraft vapour trail, once formed, will persist in ambient air which is supersaturated with respect to ice, leading to greater climate-warming impact as a result of the increase in longevity of the vapour trail.

US2010/0122519 describes the use of ultra-low sulphur aviation fuel as an alternative to conventional fuel to reduce sulphur by-product generation and hence reduce contrail formation. This document emphasises the need to retain the purity of the ultra-low sulphur aviation fuel, and hence the requirement to manage the supply chain which delivers the fuel, and to avoid mixing with other fuels.

The attempted suppression of vapour trail formation through the reduction of exhaust water vapour content through use of a heat exchanger and condenser arrangement (US2008072577A) potentially introduces significant weight into the engine.

Furthermore, the weight penalty is incurred throughout the full duration of a flight, even though vapour trail suppression may only be required for a small percentage of the flight time.

Attempted suppression of vapour trail formation through the use of directed electromagnetic energy (US2010132330A) into the engine exhaust plume could incur a weight penalty. Furthermore, the energy required to operate the system could represent a significant portion of the engine power and thus incur a fuel-burn penalty. Further, in military applications, the emission of powerful electromagnetic radiation has the undesirable effect of increasing the aircraft's detectability.

Attempted suppression of vapour trail formation through the use of ultrasound directed into the engine exhaust plume (US2010043443A) may also incur a material weight penalty associated with equipment for generating the required sound levels.

The attempted modification or suppression of vapour trails through the use of chemicals (U.S. Pat. Nos. 5,005,355A, 4,766,725A, 3,517,505A, 3,517,512A, 2009013591A) injected either into the engine (whether with the fuel or separately from the fuel) or into the exhaust plume presents the prospect of additional pollution, incurs a weight penalty through the need to carry fuel additives with potentially little or no calorific value of their own (in comparison with conventional aviation fuel when burned within the engine), and may present challenges to engine reliability and/or component life.

The attempted hiding of vapour trails through introducing black carbon into the aircraft engine effluent (U.S. Pat. No. 3,289,409A) results in additional emissions of a species (black carbon) which is known to have an environmental warming impact.

The strategy of avoiding regions prone to vapour trail formation and/or persistence through the routing of aircraft around, above and/or below such regions has the disadvantage that it increases workload for air traffic control and/or pilots, reduces airspace capacity and, in the case of routing around regions prone to vapour trail formation or persistence (which can be tens or hundreds of kilometres in horizontal extent), the length of the route followed by the aircraft is increased, resulting in a fuel-burn penalty. Additionally in the case of climbing so as to fly above regions prone to vapour trail formation or persistence, additional fuel is burned to provide the increased thrust necessary to perform the climb. If aircraft are scheduled to fly below regions prone to vapour trail formation or persistence, additional fuel may be burned subsequently if the aircraft is to return to its optimal cruising altitude once the aircraft has passed the avoided region.

In the case either of climbing so as to fly above or of descending so as to fly below regions of air susceptible to vapour trail formation and/or persistence, the aircraft will be required to fly at an altitude that may differ from the optimal cruise altitude given the aircraft's current weight. In other words, the ability of the aircraft to follow an optimal cruise-climb trajectory is hindered by the requirement to change altitude so as to avoid the region of air susceptible to vapour trail formation and/or persistence.

It is known that the climate warming impact of a vapour trail of a given horizontal extent is determined, at least in part, by its optical depth. Reductions in the number of soot particles emitted per unit mass of fuel burned by an aircraft's engine could reduce the initial optical depth of exhaust vapour trails. Hereafter in this application the number of soot particles emitted per unit mass of fuel burned is termed the "soot emission index".

Further, it is known that the production of soot from engine exhausts can be reduced through the reduction or elimination of aromatic and/or other non-paraffinic content in the fuel used. Biofuels are typically low in aromatics and/or other non-paraffinics. However, biofuels are typically much more expensive than conventional fuels and are in extremely short supply. Hence it is undesirable to fuel a vehicle with biofuel throughout its period of operation, especially as the vehicle it powers may operate for much of its time in conditions where vapour trails will not form and/or persist regardless of the fuel used.

Hence a system which reduces the optical depth of young vapour trails, therefore potentially reducing their climate warming impact, whilst optimising the use of more expensive biofuels, is highly desirable.

SUMMARY

Accordingly there is provided a fuel system comprising a vapour trail detection sensor configured to generate a first signal which indicates the optical depth of a vapour trail; a control unit responsive to the first signal and configured to generate a second signal in dependence upon the first signal which defines a percentage of at least one of a first fuel composition and second fuel composition required to produce a resultant fuel composition; and at least one regulator configured to receive and be responsive to the second signal and regulate the percentage of first and second fuel composition required to produce the resultant fuel composition.

The system provides the advantage of enabling control over vapour trail optical depth, by first identifying the presence of the vapour trail and having means to selectively control the blending together, on demand, of a first and second fuel for use in an engine. Hence a fuel composition tuned to operation requirements can be generated at the point in the usage of the engine when it is required.

BRIEF DESCRIPTION OF THE DRAWINGS

Examples of the present disclosure will now be described with reference to the accompanying drawings, in which.

DETAILED DESCRIPTION

Figure 1:
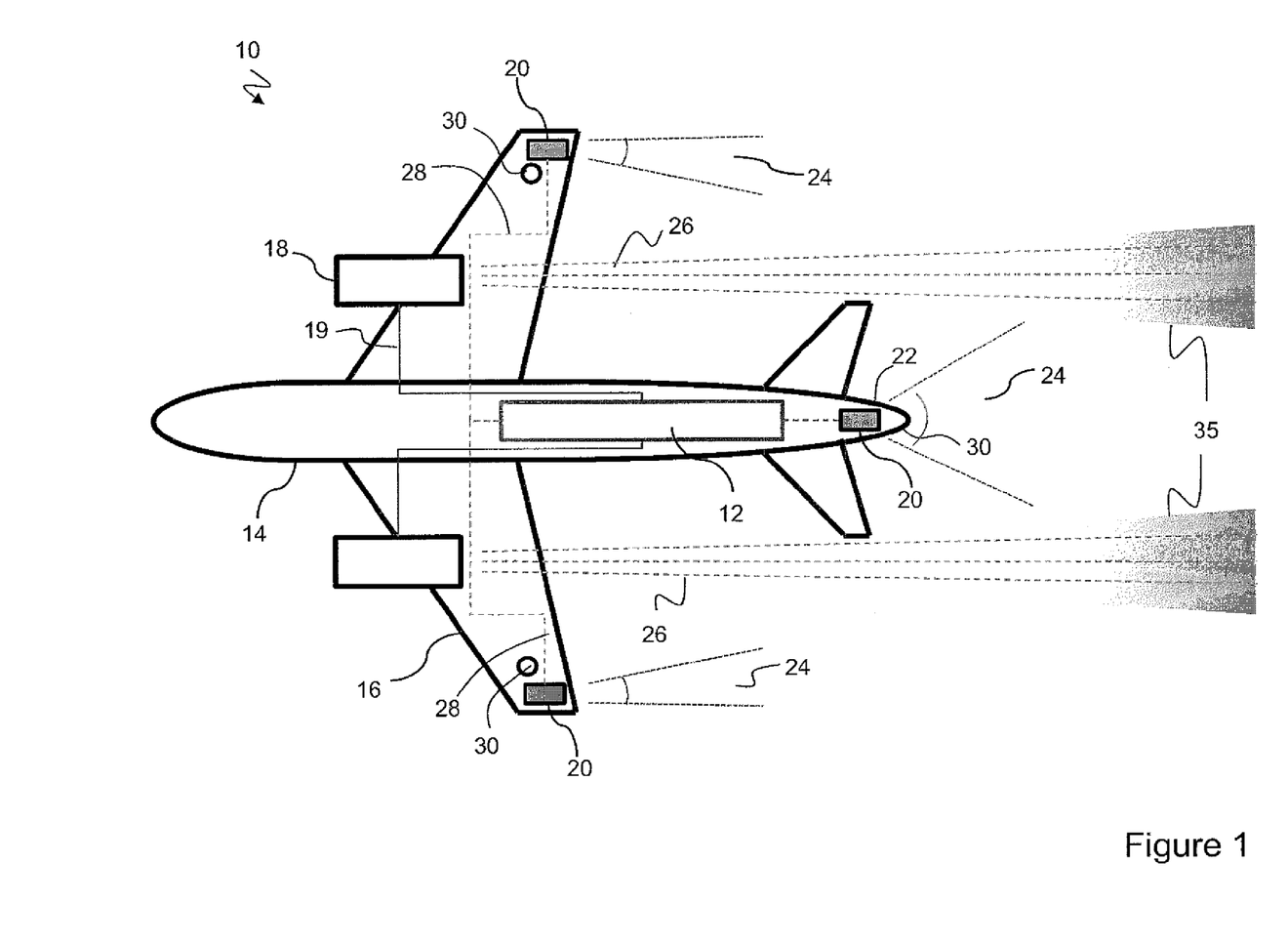
FIG. 1 shows a fuel system according to the present disclosure on an aircraft.

FIG. 1 shows a machine 10, in this example an aircraft, which comprises a fuel system 12 according to the present disclosure. In the example shown the aircraft comprises a fuselage 14 from which wings 16 extend, with engines 18 mounted to the wings. Other examples might involve alternative aircraft configurations, and different numbers of engines. The majority of the fuel system 12 is shown located in the fuselage 14. In alternative examples the fuel system 12 may be located elsewhere in the machine 10. Fuel pipes 19 fluidly connect the fuel system 12 and engines 18.

The fuel system 12 comprises at least one vapour trail detection sensor 20. In the example shown in FIG. 1, vapour trail detection sensors 20 are mounted towards the rear of the aircraft 10 facing aft. For example they are located at the tip of both wings 16 and at a trailing edge 22 of the fuselage. The vapour trail detection sensor 20 is mounted such that it has a field of view directed towards a vapour trail formation region. That is to say they are positioned such that they have a field of view 24 in a direction downstream of the vehicle 10, which in operation will offer a view of vapour trails 35 formed within the exhaust plume 26 downstream of the engines 18. Each of the vapour trail detection sensors 20 is configured to generate a first signal 28 (shown as a dotted line) which indicates an optical depth of the young vapour trail 35.

Each vapour trail detection sensor 20 is an optical device configured to deliver a signal indicative of the presence and/or properties of a vapour trail 35. A source of illumination 30 may also be provided on the aircraft and directed towards at least one region downstream of the engines 18 to illuminate at least part of the field of view 24 of the sensor 20. The sensor 20 is configured to detect electromagnetic radiation of at least one wavelength emitted and/or reflected by the vapour trail in response to energy emitted from the source of illumination 30.

In an alternative embodiment, the function of the vapour trail detection sensor would be performed by equipment remote to the aircraft, and the resulting information transmitted to the aircraft. Such equipment might include for example sensors mounted on the ground, on airships, on other aircraft, or on earth-orbiting satellites. In such situations, the operation of the non-aircraft mounted vapour-trail detection sensors may optionally be enhanced by use of the aircraft-mounted source of illumination 30.

Figure 2:
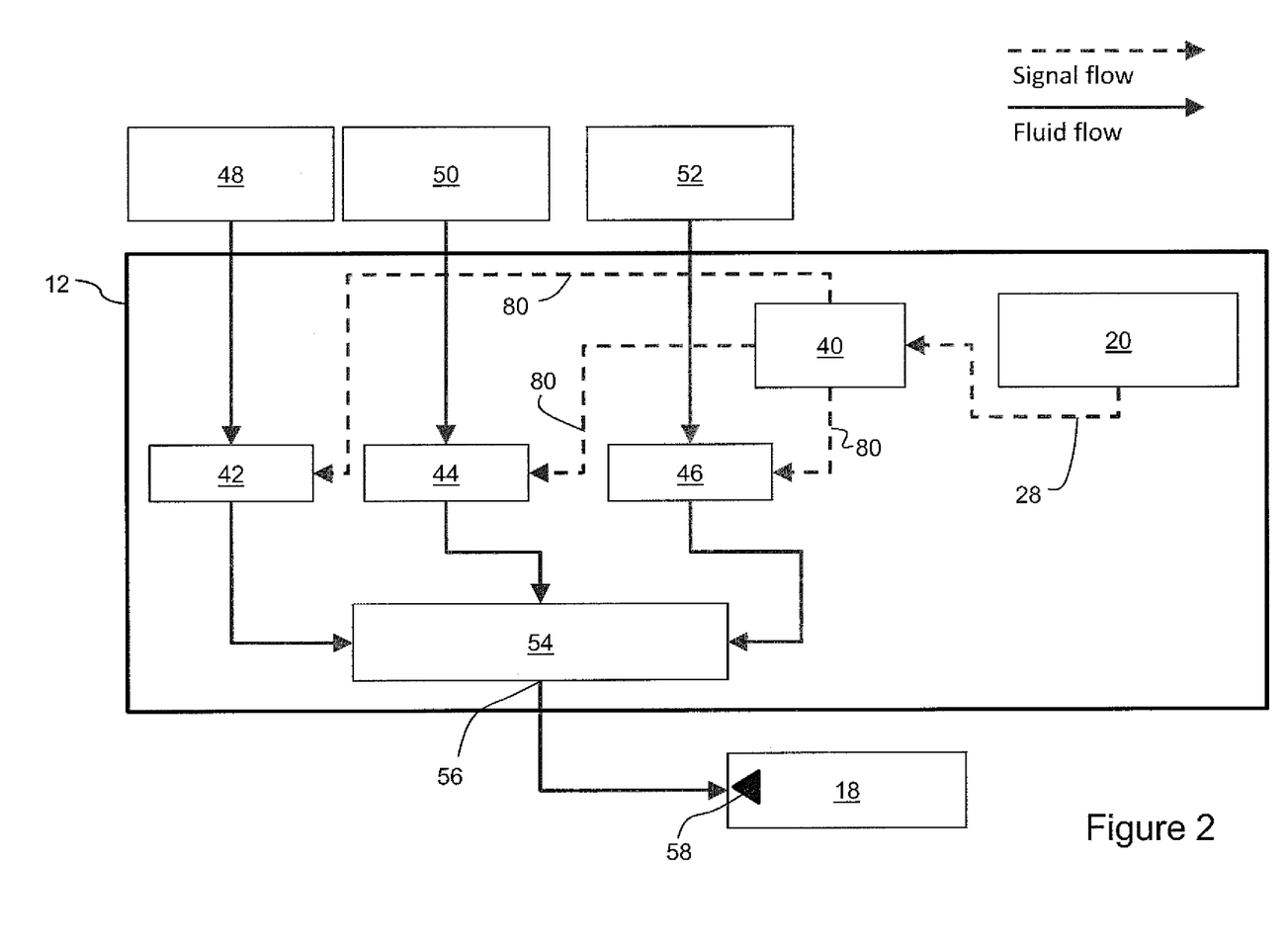
FIG. 2 is a diagrammatic representation of the fuel system of the present disclosure.

FIG. 2 shows a diagrammatic representation of the fuel system 12. For the avoidance of doubt, and as also shown in FIG. 1, the arrows with solid lines indicate the fuel flow communication path, and the arrows with dashed lines indicate signal communication routes.

The fuel system 12 has a control unit 40 which is in signal communication with the or each vapour trail detection sensor(s) 20. In FIG. 2 only one vapour trail detection sensor 20 is shown. In alternative examples there may be more than one sensor 20.

The control unit 40 is also in signal communication with at least a first fuel composition regulator 42 and a second fuel composition regulator 44. In FIG. 2 a third fuel composition regulator 46 is shown. The number of fuel composition regulators is dependent upon the number of fuel compositions the system is configured to operate with. Each fuel composition regulator 42,44,46 is in fluid flow communication with a source 48, 50, 52 of its respective fuel composition. The source of the first fuel composition is a first tank 48 for storage of a first fuel composition, and the source of the second fuel composition is a second tank 50 for storage of a second fuel composition. In the example shown the source of the third fuel composition is a third tank 52 for storage of a third fuel composition. Further tanks are a source of the fuel composition that they are provided to contain. The tanks 48,50,52 are located on board the aircraft 10. The tanks 48, 50, 52 etc are fluidly isolated from one another. That is to say, the tanks 48, 50, 52 are not in fluid communication with each other, and there is no flow of fluid between them. The word "tank" is intended to mean an individual tank or a network of fluidly interconnected tanks, where each network is fluidly isolated from the other networks.

The fuel system 12 further comprises a fluid blender 54 in fluid communication with the source 48 of the first fuel composition, the source 50 of the second fuel composition etc via the regulators 42,44,46. The blender 54 is configured to mix the first fuel composition, second fuel composition etc to produce a resultant fuel composition.

The fluid blender 54 has at least one outlet 56 for delivering the resultant fuel composition to a fuel injection device 58 in the engine(s) 18. The fuel injection device 58 may be any type of fuel injector, for example a fuel nozzle, airspray injector, or plain orifice. The fuel injection device 58 may comprise one fuel injector, or a plurality of fuel injectors. Although in FIG. 2 and FIG. 3 only one fuel injector 58 is shown, each engine 18 may be fitted with a number of fuel injectors 58, each in fluid communication with the fuel blender 54.

Figure 3:
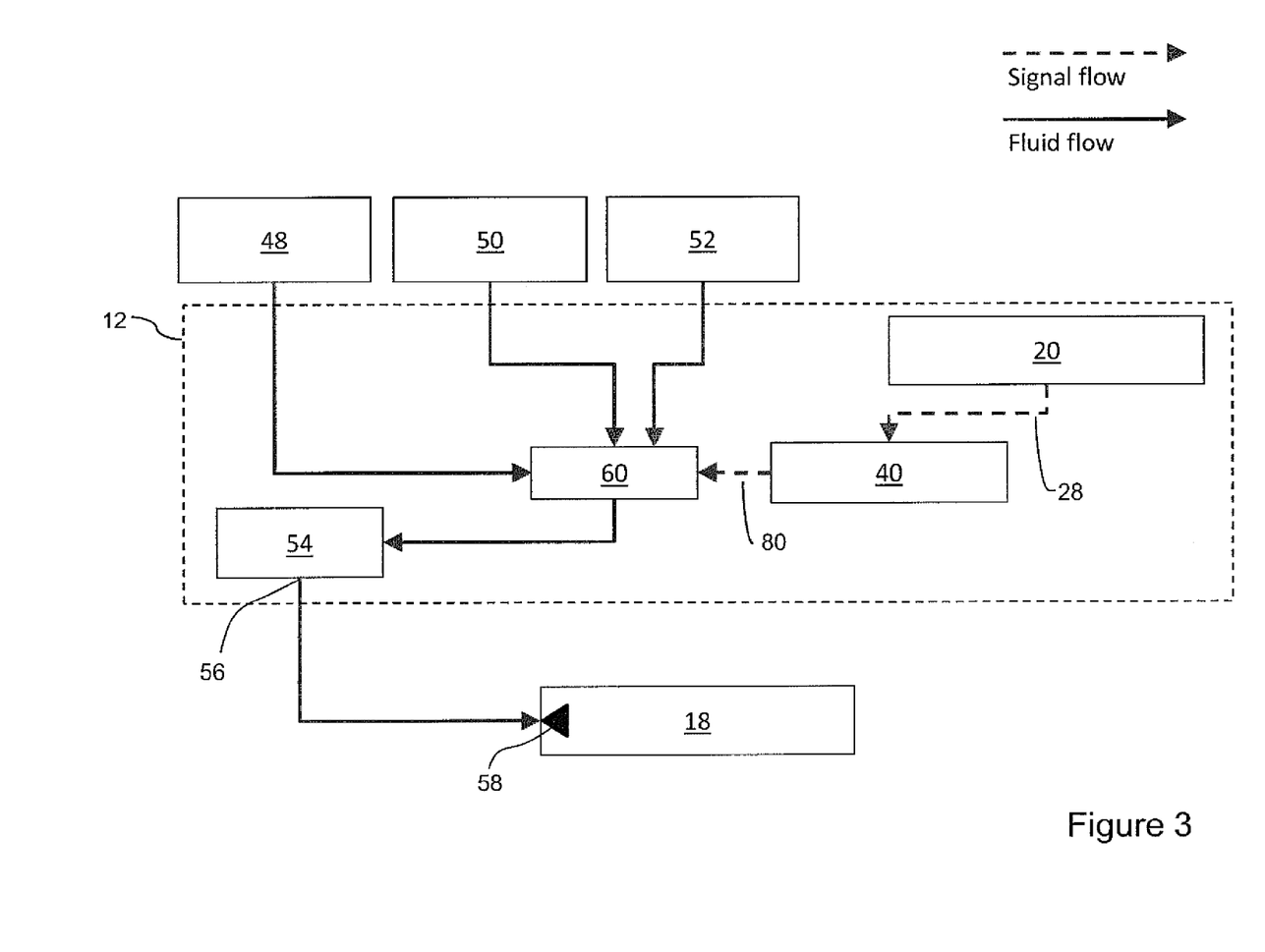
FIG. 3 is an alternative example to that shown in FIG. 2.

FIG. 3 shows a diagrammatic representation of an alternative example of the fuel system 12 according to the present disclosure. Features common to the example shown in FIG. 2 share the same reference numerals. The only difference between the examples is that instead of a regulator 42,44,46 for each fuel composition, there is a single regulator 60 which is in fluid communication with all of the fluid tanks 48,50,52.

Figure 4:
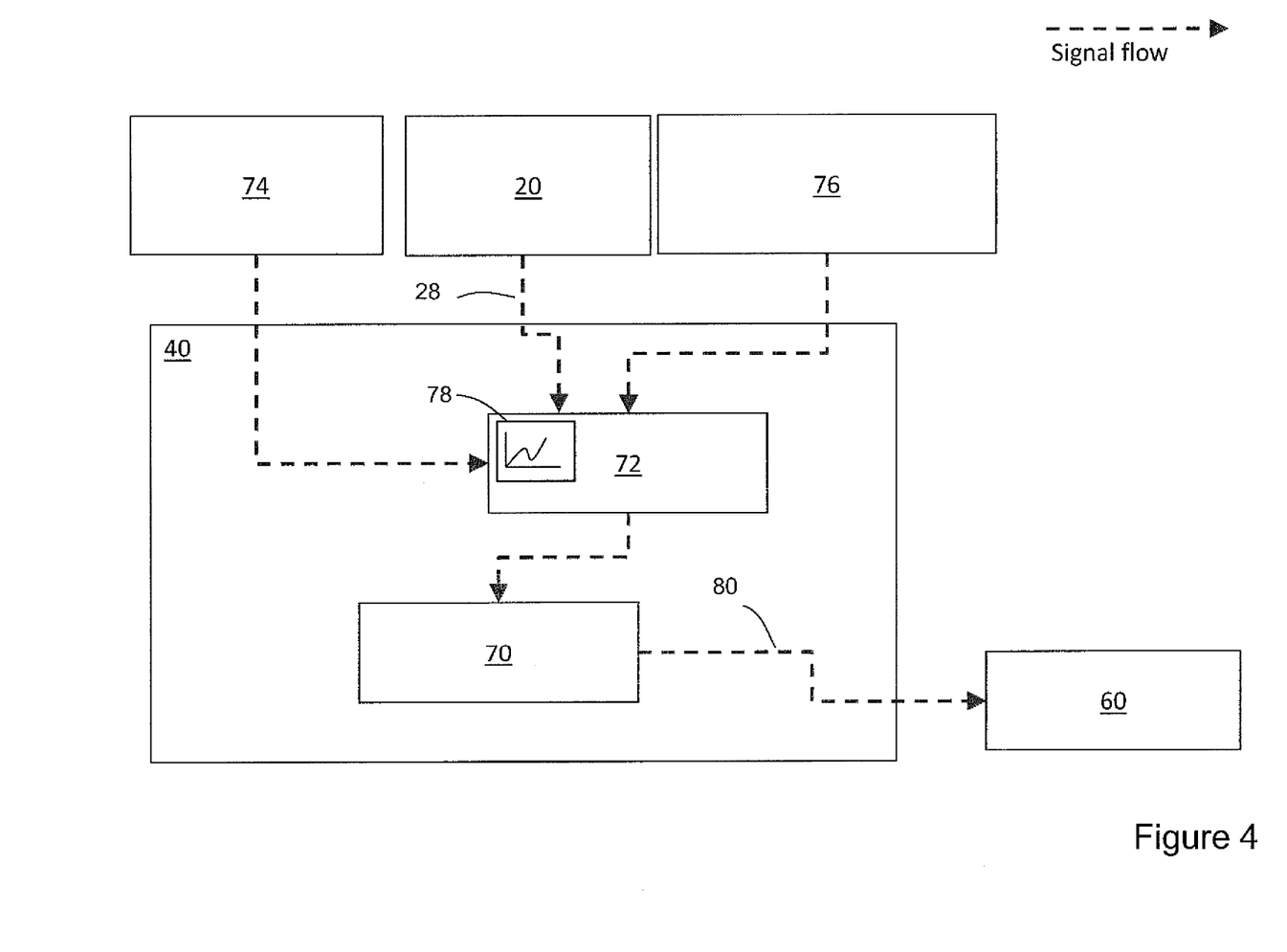
FIG. 4 is a diagrammatic representation showing further detail of the fuel system of the present disclosure.

As shown diagrammatically in FIG. 4, the control unit 40 comprises a blending ratio calculator 70 configured to calculate the required resultant fuel composition as a function of desired soot emission index determined by a soot requirement generator 72 which communicates the desired value of soot emission index to the blending ratio calculator 70.

The soot requirement generator 72 is in signal communication with the vapour trail detection sensor 20. It is also in signal communication with an array of sensors 74 for detecting (e.g. measuring) ambient temperature, ambient pressure, ambient humidity and/or instantaneous actual values of soot emission index generated by the engine(s) 18. The soot requirement generator 72 is also optionally in signal communication with an array of sensors 76 or monitors for determining engine operating point. The engine operating point is defined by a collection of parameters including the ambient conditions in which the engine is operating, as well as for example one or more of fuel-flow rate, temperatures and pressures of the gas-flow at various parts of the engine, thrust produced by the engine, and other parameters indicative of the state of the engine.

The soot requirement generator 72 also comprises, or is linked to, a look up table or database 78 for determining the desired soot emission index. The look up table or database 78 comprises data relating to the dependency of vapour trail optical depth upon soot emission index at various ambient conditions. Alternatively, or additionally, the soot requirement generator 72 comprises a model and/or algorithm for direct calculation of the desired soot emission index.

Alternatively or additionally, the soot requirement generator may attempt to reduce the observed vapour trail optical depth by adjusting in an iterative fashion the desired soot emission index in response to the signal 28 indicative of the vapour trail optical depth.

The soot requirement generator 72 may optionally take account of constraints which limit the achievable range of soot emission index at the particular engine operating point and ambient air condition, given the types of fuel available to it. In so doing, the soot requirement generator 72 would be able to avoid specifying a soot emission index which could not be achieved in practice.

The fuel system 12 may further comprise a vapour trail modelling tool configured to first determine ambient air conditions in dependence upon actual measured values of ambient air conditions, and then to determine the likelihood of vapour trail formation and/or vapour trail persistence based on engine operating point and the ambient air conditions.

In operation the control unit 40 receives the first signal 28 and determines the optical depth of a vapour trail 35 being generated by the engine(s) 18. The soot requirement generator 72 determines a value of desired soot emission index which would generate optimal vapour trail optical depth for given ambient conditions and engine operating point. The soot requirement generator 72 is in communication with the various previously described sensor means 20,74, 76 and receives the one or more measured values from each sensor or array of sensors 20,74,76. The soot requirement generator 72 calculates the desired soot emission index as a function of one or more of the values measured by the sensors and sensor arrays (for example ambient temperature, ambient pressure, ambient humidity and/or vapour trail optical depth received from the sensors 20,74,76.) In dependence upon the calculated desired soot emission index, the blending ratio calculator 70 then generates a second signal 80 which defines a percentage of the first fuel composition, second fuel composition etc to be blended together to produce a resultant fuel composition. The regulator 60 (or regulators 42,44,46) receives and is responsive to the second signal 80 to regulate the percentage of the individual fuel compositions which are blended together to produce the resultant fuel composition.

In the context of the present disclosure, "optimal" soot emission index is the soot emission index which, if realised in practice under the prevailing ambient conditions, would lead to a minimisation of optical depth of the young contrail, and hence a minimisation of a young contrail's climate warming impact. Under some ambient conditions the "optimal" soot emission index may correspond to the minimum achievable soot emission index given the available fuels and any constraints that may place limits on the blending ratios that may be employed. Alternatively, under other ambient conditions, the "optimal" soot emission index may be higher than or lower than the minimum achievable soot emission index.

The first fuel composition may have an aromatic and/or other non-paraffinic content substantially higher than that of the second fuel composition. In one example the first fuel composition is Kerosene. Additionally or alternatively the second fuel composition is a biofuel. The second fuel composition may be a low-soot-producing (LSP) or alternatively a low-sulphur, low-soot-producing (LSLSP) fuel. Alternatively or additionally the second fuel may be a blend of several such LSP and/or LSLSP fuels whose physical and chemical properties make it suitable for use in an engine with the first fuel composition, for example as an aviation fuel when blended with conventional kerosene. Examples include (but are not limited to) coal-to-liquids (CTL), gas-to-liquids(GTL), biomass-to-liquids (BTL), synthetic paraffinic kerosene (SPK), hydrotreated renewable jet-fuel (HRJ), alcohol-to-jet, and Hydro-processed Esters and Fatty Acids (HEFA).

The system 12 is operable to blend fuel, or to simply deliver one of the stored fuel compositions. That is to say the action of blending together two or more fuels may optionally be employed or not employed according to policy decision taking account of ambient conditions and engine operating point. The resultant fuel composition may comprise any proportion of first fuel composition and second fuel composition in the range from 0% to 100%. The resultant fuel composition may comprise x % of the first fuel composition and (100−x)% of the second fuel composition, where x has a value anywhere in the range from 0 to 100. For example, the resultant fuel composition may comprise 0% of the first fuel composition and 100% of the second fuel composition. Alternatively the resultant fuel composition may comprise 100% of the first fuel composition and 0% of the second fuel composition. Additionally x may have a value greater than 0 and less than 100.

The control unit 40 may determine which of a default fuel composition and a composition which may enable the optical depth of the vapour trail to be reduced is employed. This determination may be based on the determined likelihood of contrail formation and/or persistence, and taking into account an operational policy specifying the conditions under which vapour trail optical-depth modification should be attempted.

In an alternative example the resultant fuel composition may comprise a % of the first fuel composition, b % of the second fuel composition and c % of additional fuel or additive compositions, where a+b+c=100%, and a, b or c may have a value anywhere in the range from 0 to 100.

For example in the absence of vapour trail formation, it may be desirable to use only one of the first or second fuel compositions, and hence the resultant fuel composition will simply be the first or second fuel composition. For example 100% kerosene may be delivered to the engines 18 via the fuel injectors 58, rather than a blend of kerosene and biofuel. Alternatively where the ambient conditions are such that vapour trails form but do not persist (i.e. in ambient air not super-saturated with respect to ice), the system could be operated or not operated, depending on the extent to which the occurrence of temporary vapour trails is considered desirable or not, and taking account of the available quantity of biofuel. Additionally if the engine is operating near, but not in, a region of ice-supersaturation and it was predicted that prevailing winds may direct exhaust soot into the area of ice-super-saturation, the system may be operated to produce a soot emission index that will reduce the impact of the emitted soot upon the optical density of any cloudiness in the said nearby region. However, in situations where vapour trails form and persist, it is envisaged that the system would operate so as to reduce the optical depth of the "young" vapour trail.

The system herein described is thus advantageous since it enables control over vapour trail optical depth by selectively blending together on demand (for example) a conventional fuel together with a fuel characterised by low levels of aromatic and/or other non-paraffinic content for use in an engine to optimise soot emission index in the products of combustion from the engine. Thus one of the fuels (for example a fuel characterised by low levels of aromatic and/or other non-paraffinic content) need only be used during part of the operation of the engine. This is of particular benefit as such fuels tend to be more expensive to produce. Thus the system of the present invention enables reduction of the optical depth, and hence the climate warming impact, of vapour trails in a cost effective manner.

The device/method of the present disclosure has little weight penalty, little power requirements in usage, and maximises the climate benefits of a given volume of, for example, biofuel.

In examples where the system of the present disclosure is used as part of an aircraft, i.e. to deliver fuel to aircraft engines, the aircraft need not avoid unfavourable altitudes at which vapour trails would be unavoidable for an aircraft burning conventional fuel (e.g. kerosene), and hence will tend to travel less distance, and tend to travel at favourable altitudes, thereby minimising its overall fuel consumption. Furthermore such a system avoids any loss of airspace capacity because it reduces the climate warming impact associated with aviation induced cloudiness formed whilst cruising within ice-supersaturated regions. In other words the device/method of the present disclosure enables the aircraft to follow an optimal cruise-climb trajectory, whilst minimising the resulting vapour-trail related climate impact.

Thus the device/method of the present disclosure maximises climate benefit for a given expenditure on alternative fuels.

In examples where the system of the present disclosure is applied to marine vessels, it could enable the reduction of vapour trails generated from the vessels exhaust, sometimes referred to as "ship tracks".

Hence the system of the present disclosure will enable vehicles (aircraft, marine etc) to reduce vapour trail optical depth, thus increasing their envelope of operation for a given level of environmental impact.

The invention claimed is:

1. A fuel system comprising:
    a vapor trail detection sensor configured to generate a first signal which indicates an optical depth of a vapor trail;
    a control unit responsive to the first signal and configured to generate a second signal in dependence upon the first signal which defines a percentage of at least one of a first fuel composition and a second fuel composition required to produce a resultant fuel composition; and
    at least one regulator configured to receive and be responsive to the second signal and regulate the percentage of the at least one of the first fuel composition and the second fuel composition required to produce the resultant fuel composition that controls the optical depth of the vapor trail,
    wherein the control unit comprises a blending ratio calculator configured to calculate the required resultant fuel composition as a function of desired soot emission index determined by a soot requirement generator which communicates a value of soot emission index to the blending ratio calculator.

2. A fuel system as claimed in claim 1 wherein the control unit is operable to determine a likelihood of persistence of the vapor trail and determine the resultant fuel composition in dependence upon the determined likelihood of persistence of the vapor trail.

3. A fuel system as claimed in claim 1 further comprising a fluid blender in fluid communication with a source of the first fuel composition and a source of the second fuel composition via the at least one regulator, the blender being configured to mix the at least one of the first fuel composition and the second fuel composition to produce the resultant fuel composition.

4. A fuel system as claimed in claim 1 wherein the vapor trail detection sensor is an optical device configured to deliver a signal indicative of a presence and/or properties of the vapor trail.

5. A fuel system as claimed in claim 1 comprising a source of illumination, the vapor trail detection sensor being configured to detect electromagnetic radiation of at least one wavelength emitted and/or reflected by the vapor trail in response to energy emitted from the source of illumination.

6. A fuel system as claimed in claim 1 wherein a source of the first fuel composition is a first tank for storage of the first fuel composition;
    a source of the second fuel composition is a second tank for storage of the second fuel composition; and
    the first tank and second tank are fluidly isolated from one another.

7. A fuel system as claimed in claim 3 wherein the fluid blender has at least one outlet for delivering the resultant fuel composition to an engine fuel injector.

8. A fuel system as claimed in claim 1 wherein the soot requirement generator is configured to calculate the desired soot emission index as a function of one or more of vapor trail optical depth and/or measured values of ambient temperature, ambient pressure and/or ambient humidity.

9. A fuel system as claimed in claim 8 wherein the soot requirement generator is in communication with the vapor trail detection sensor to receive vapor trail optical depth data and/or a sensor to receive the one or more measured values.

10. A fuel system as claimed in claim 1 wherein the soot requirement generator is in communication with a second sensor to receive a value for instantaneous measured actual values of soot emission index generated by an engine.

11. A fuel system as claimed in claim 1 wherein the soot emission index is derived from a look up table or database in dependence upon one or more of the first fuel composition and the second fuel composition, combustion characteristics of an engine and/or engine operating point.

12. A fuel system as claimed in claim 1 wherein the soot requirement generator determines a value of desired soot emission index which would generate optimal vapor trail optical depth for given ambient conditions and engine operating point.

13. A fuel system as claimed in claim 1 wherein the soot requirement generator comprises a model and/or algorithm for direct calculation of the desired soot emission index.

14. A fuel system as claimed claim 1 comprising a vapor trail modeling tool configured to first determine ambient air conditions in dependence upon actual measured values of ambient air conditions, and then to determine the likelihood of vapor trail formation and/or vapor trail persistence based upon engine operating point and the determined ambient air conditions.

15. A fuel system as claimed in claim 14 further comprising a comparator for comparing output from the vapor trail modeling tool with an instantaneous actual vapor trail observation to determine the effect of the resultant fuel composition on vapor trail formation and/or vapor trail persistence.

16. An aircraft comprising a fuel system as claimed in claim 1, wherein the vapor trail detection sensor is mounted towards a rear of an aircraft facing aft.

17. An aircraft as claimed in claim 16 comprising an engine, the vapor trail detection sensor mounted such that it has a field of view directed towards a vapor trail formation region.

18. An aircraft as claimed in claim 17 wherein a source of illumination is directed towards at least one region downstream of the engine.

* * * * *